United States Patent
Asafusa et al.

(10) Patent No.: US 8,517,948 B2
(45) Date of Patent: Aug. 27, 2013

(54) ULTRASOUND DIAGNOSTIC APPARATUS AND METHOD OF CALIBRATING THE SAME

(75) Inventors: Katsunori Asafusa, Tokyo (JP); Tatsuya Nagata, Hitachinaka (JP)

(73) Assignee: Hitachi Medical Corporation, Tokyo (JP)

( * ) Notice: Subject to any disclaimer, the term of this patent is extended or adjusted under 35 U.S.C. 154(b) by 745 days.

(21) Appl. No.: 12/093,987

(22) PCT Filed: Oct. 25, 2006

(86) PCT No.: PCT/JP2006/321228
§ 371 (c)(1),
(2), (4) Date: Aug. 11, 2009

(87) PCT Pub. No.: WO2007/058056
PCT Pub. Date: May 24, 2007

(65) Prior Publication Data
US 2009/0299192 A1    Dec. 3, 2009

(30) Foreign Application Priority Data
Nov. 18, 2005 (JP) ................ 2005-333797

(51) Int. Cl.
*A61B 8/14* (2006.01)
(52) U.S. Cl.
USPC ........................................... 600/459
(58) Field of Classification Search
None
See application file for complete search history.

(56) References Cited

U.S. PATENT DOCUMENTS

| | | | |
|---|---|---|---|
| 3,518,536 A * | 6/1970 | Shih-Ying et al. | 324/609 |
| 6,328,696 B1 | 12/2001 | Fraser | |
| 6,451,015 B1 * | 9/2002 | Rittman et al. | 606/34 |
| 6,632,178 B1 * | 10/2003 | Fraser | 600/459 |
| 2002/0093581 A1 * | 7/2002 | Ikeda et al. | 348/302 |
| 2004/0122325 A1 * | 6/2004 | Chambers et al. | 600/467 |
| 2005/0200241 A1 * | 9/2005 | Degertekin | 310/334 |
| 2005/0219953 A1 * | 10/2005 | Bayram et al. | 367/178 |

FOREIGN PATENT DOCUMENTS

| | | |
|---|---|---|
| JP | 2004-503312 | 2/2004 |
| JP | 2004-274756 | 9/2004 |

OTHER PUBLICATIONS

Bayram, et al., "Capacitive Micromachined Ultrasonic Transducer Design for High Power Transmission", IEEE Transations, Feb. 2005, vol. 52, No. 2, ISSN 0885-3010, http://www.ieee-uffc.org/tr/.

* cited by examiner

*Primary Examiner* — Long V. Le
*Assistant Examiner* — Bo J Peng
(74) *Attorney, Agent, or Firm* — Antonelli, Terry, Stout & Kraus, LLP.

(57) ABSTRACT

An ultrasound diagnostic apparatus 1 causes discharge means 4 to apply a discharge pulse (having a peak value equal to or greater than a collapse voltage) between electrodes of an ultrasound transducer 20 a plurality of time while inverting the polarity of the discharge pulse each time, to thereby accelerate discharge of the charge accumulated in the diaphragm of the ultrasound transducer 20, so that a transmission-reception sensitivity offset can be caused to quickly approach zero. The charge is discharged instantaneously. That is, it is possible to quickly calibrate a transmission-reception sensitivity drift stemming from time-course accumulation of charge flowing into the diaphragm between the electrodes upon application of a DC bias thereto.

17 Claims, 11 Drawing Sheets

| DATE | TIME | APPLICATION TIME | APPLICATION VOLTAGE | SUM OF PRODUCT | STATE |
|---|---|---|---|---|---|
| 2006/9/12 | 10:00~12:00 | 2h | 100V | 200V·h | 0.67% |
| 2006/9/12 | 9:30~17:30 | 8h | 100V | 1000V·h | 3.33% |
| ⋮ | ⋮ | ⋮ | ⋮ | ⋮ | ⋮ |
| 2006/12/14 | 10:00~17:00 | 7h | 100V | 30000V·h | 100% |
| 2006/12/14 | 17:30 | - | - | - | DISCHARGE |
| 2006/12/15 | 10:00~13:00 | 3h | 100V | 300V·h | 1.00% |
| ⋮ | ⋮ | ⋮ | ⋮ | ⋮ | ⋮ |

ULTRASOUND DIAGNOSTIC APPARATUS AND METHOD OF CALIBRATING THE SAME

TECHNICAL FIELD

The present invention relates to an ultrasound diagnostic apparatus equipped with an ultrasound probe in which a DC bias is applied between electrodes thereof and which transmits and receives ultrasound waves, and to a method of calibrating such an ultrasound diagnostic apparatus.

The present application claims priority benefits of Paris Convention from Japanese Patent Application No. 2005-333797 duly filed under the Japanese Patent Law, the contents of which are incorporated herein by reference.

BACKGROUND ART

Conventionally, a capacitive micro-machined ultrasound transducer (cMUT) has been manufactured through use of a semiconductor deposition technique. The cMUT is a very small diaphragm-like device which includes electrodes for converting a sonic vibration of an ultrasound signal to a modulated capacitance. The cMUT has a sacrificial layer between the electrodes. A DC bias and AC pulses are applied between the electrodes so as to modulate a capacitance charge to thereby generate an electric field, so that a diaphragm vibrates and thus an ultrasound wave is generated.

Further, there has been proposed a capacitive micro-machined ultrasound transducer (cMUT) whose capacitance is monitored by means of a capacitance regulator so as to adjust a bias charge thereof. The capacitance regulator measures a minute AC voltage stemming from charging or discharging at a diaphragm electrode to thereby measure the capacitance of the cMUT. Thus, the bias charge is produced and maintained (see, for example, "Patent Document 1").

Patent Document 1: Japanese kohyo (PCT) Patent Publication No. 2004-503312

DISCLOSURE OF THE INVENTION

Problems to be Solved by the Invention

However, such a cMUT has, between the electrodes, not only a sacrificial layer, but also a diaphragm which prevents formation of a short circuit and has a conductivity of about $10^{11}$ to $10^{14}$ Ω/m, and a rim for providing a vertical clearance between the electrodes. Therefore, such a cMUT has a problem in that when a DC bias is applied between the electrodes, a leak current flows (a charge moves) into the diaphragm and the rim between the electrodes in accordance with the impedance thereof in a circuit determined by the conductivity, shape, etc., although the leak current is slight.

In particular, once injection of a charge into the diaphragm occurs, due to influence of the inter-electrode field intensity, the sensitivity associated with transmission and reception of ultrasound waves (hereinafter referred to as "transmission-reception sensitivity") changes with time. Further, the charge injected into the diaphragm remains within the diaphragm even after the application of the DC bias is interrupted. Due to application of the DC bias over a long period, charge accumulates in the diaphragm, and the charge accumulated in the diaphragm causes a drift in the sensitivity associated with transmission and reception of ultrasound waves (hereinafter referred to as "transmission-reception sensitivity drift"), resulting in generation of a transmission-reception sensitivity distortion. The transmission-reception sensitivity distortion causes an increase in harmonic components.

In the technique disclosed in "Patent Document 1" and "Patent Document 2," charging or discharging occurs at the electrodes. However, such charging or discharging does not remove the charge injected into an insulating portion between the electrodes. Therefore, the disclosed technique has a problem in that it cannot suppress transmission-reception sensitivity distortion stemming from the above-described transmission-reception sensitivity drift.

The present invention has been accomplished in view of the above-described problems, and an object of the present invention is to provide an ultrasound diagnostic apparatus which quickly calibrates a transmission-reception sensitivity drift stemming from time-course accumulation of charge flowing into an insulating portion between electrodes upon application of a DC bias thereto.

Means for Solving the Problems

In order to achieve the above-described object, according to a first invention, there is provided an ultrasound diagnostic apparatus comprising an ultrasound probe equipped with an ultrasound transducer including a pair of electrodes and an insulating portion and a sacrificial layer provided between the electrodes; DC-bias application means for applying a DC bias between the electrodes; transmission means for causing a portion of the insulating portion to vibrate through application of an ultrasound transmission pulse between the electrode in addition to the DC bias, to thereby transmit an ultrasound wave toward a subject; reception means for receiving an ultrasound echo from the subject; and image-processing means for producing an ultrasound image on the basis of a signal output from the reception means, the ultrasound diagnostic apparatus being characterized by further comprising discharge means for discharging a charge accumulated in the insulating portion between the electrodes.

The ultrasound diagnostic apparatus is configured such that any charge which is accumulated in the insulating portion between the electrodes as a result of application of a DC bias over a long time is discharged through application of a predetermined voltage between the electrodes of the ultrasound transducer at least one time such that the polarity of the voltage is inverted repeatedly.

With this operation, the ultrasound diagnostic apparatus accelerates discharge of the charge accumulated in the insulating portion between the electrodes, so that the transmission-reception sensitivity offset quickly approaches zero. That is, the ultrasound diagnostic apparatus can quickly calibrate a transmission-reception sensitivity drift stemming from time-course accumulation of charge which flows into a diaphragm between electrodes upon application of a DC bias thereto.

Preferably, the discharge means accelerates the discharge of the charge through application of a voltage between the electrodes, the voltage being equal to or higher than a collapse voltage.

With this, a collapse phenomenon occurs in the ultrasound transducer, and the gap width of the sacrificial layer becomes zero. As a result, the impedance decreases sharply, so that the charge discharge speed increases. The discharge of charge takes place instantaneously.

According to a second invention, there is provided a method of calibrating an ultrasound diagnostic apparatus comprising an ultrasound probe equipped with an ultrasound transducer including a pair of electrodes and an insulating portion and a sacrificial layer provided between the electrodes, and DC-bias application means for applying a DC bias between the electrodes, the method being characterized by comprising a monitor step of monitoring an amount of charge accumulated in the insulating portion between the electrodes; a discharge step of discharging the charge accumulated in the insulating portion between the electrodes on the basis of the amount of charge; and a step of repeating the monitor step and the discharge step.

Effect of the Invention

According to the present invention, it is possible to provide an ultrasound diagnostic apparatus which quickly calibrates a transmission-reception sensitivity drift stemming from time-course accumulation of charge flowing into an insulating portion between electrodes upon application of a DC bias thereto.

Figure 1:
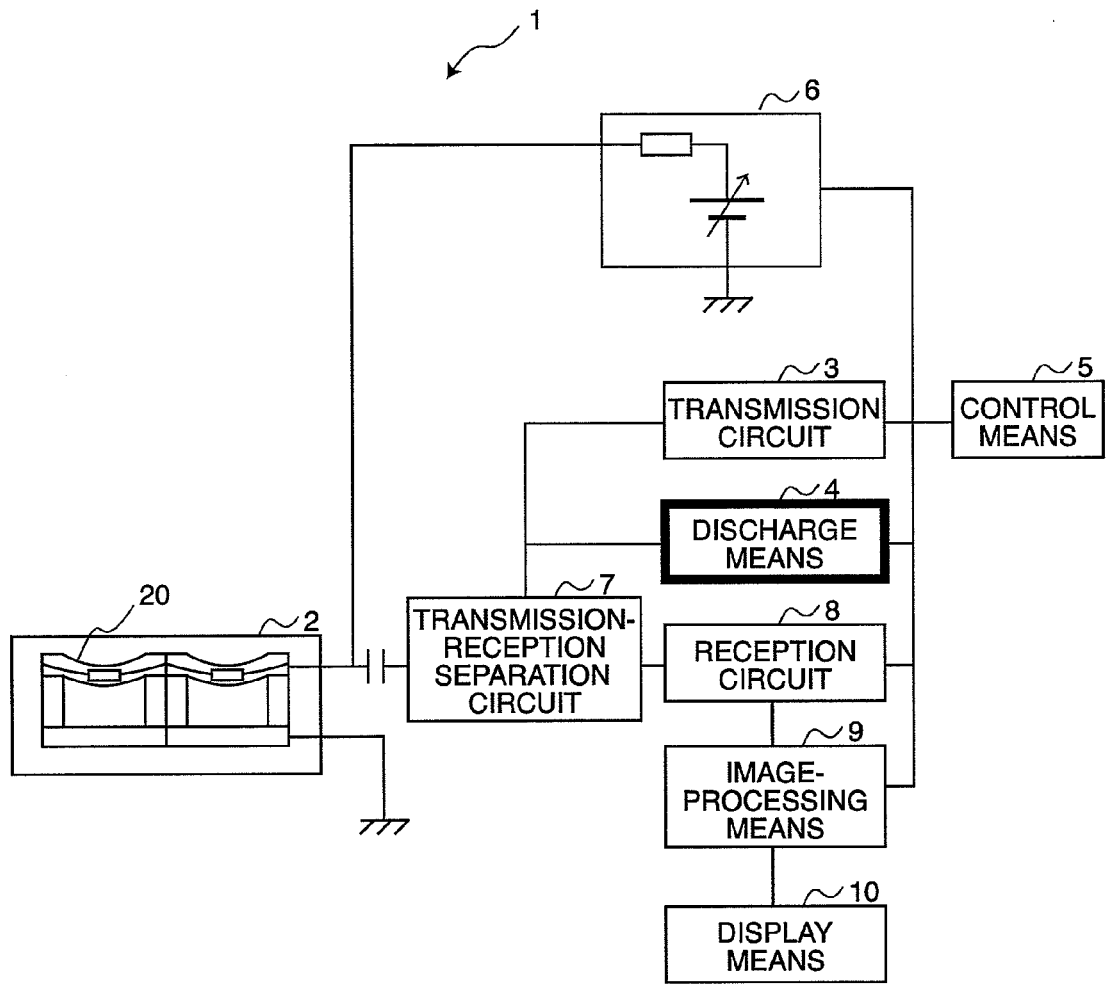
FIG. 1 Schematic configurational diagram of an ultrasound diagnostic apparatus 1 (first embodiment).

DESCRIPTION OF REFERENCE NUMERALS 1, 1a, 1b, 1c . . . ultrasound diagnostic apparatus
2 . . . ultrasound probe
3, 3a . . . transmission circuit
4, 4a, 80 . . . discharge means
5 . . . control means
6, 6b . . . DC bias circuit
7 . . . transmission-reception separation circuit
8 . . . reception circuit
9 . . . image-processing means
10 . . . display means
20, 60, 70 . . . ultrasound transducer
21, 61, 71 . . . upper electrode
22 . . . diaphragm
23 . . . rim
24, 62, 72 . . . lower electrode
25, 64, 74 . . . sacrificial layer
27 . . . gap width
31 . . . ultrasound transmission pulse timing generation means
32 . . . ultrasound transmission pulse waveform producing means
33 . . . ultrasound transmission pulser
41 . . . discharge pulse timing generation means
42 . . . discharge pulse waveform producing means
43 . . . discharge pulser
51 . . . computation section
52 . . . main memory
53 . . . storage section
54 . . . applied bias historical information
55 . . . discharge pulse waveform information
56 . . . state transition information
63, 73 . . . insulating portion
69, 79 . . . charge injection
151, 155 . . . communication section
152 . . . network
153 . . . external control apparatus
154 . . . remote maintenance center
159 . . . historical information
160 . . . storage section

BEST MODE FOR CARRYING OUT THE INVENTION

A preferred embodiment of an ultrasound diagnostic apparatus according to the present invention will next be described in detail with reference to the attached drawings. In the following description and the attached drawings, structural elements having generally identical functional configurations are denoted by like reference numerals, and their repeated descriptions are omitted.

(1. Configuration of an Ultrasound Diagnostic Apparatus 1)

First, an ultrasound diagnostic apparatus 1 according to a first embodiment of the present invention will be described with reference to FIGS. 1 to 5.

(1-1. Schematic Configuration of The Ultrasound Diagnostic Apparatus 1)

FIG. 1 is a schematic configurational diagram of the ultrasound diagnostic apparatus 1.

The ultrasound diagnostic apparatus 1 is composed of an ultrasound probe 2, a transmission circuit 3, discharge means 4, control means 5, a DC bias circuit 6, a transmission-reception separation circuit 7, a reception circuit 8, image-processing means 9, and display means 10.

The ultrasound diagnostic apparatus 1 of the first embodiment employs a configuration in which respective outputs of the transmission circuit 3 and the discharge means 4 are fed to the transmission-reception separation circuit 7 after being combined together.

The ultrasound diagnostic apparatus 1 transmits ultrasound waves to a subject and receives ultrasound waves from the subject by means of the ultrasound probe 2, and performs image processing by means of the image-processing means 9 so as to output a captured image of the subject to the display means 10. The ultrasound diagnostic apparatus 1 applies a DC bias between electrodes of each ultrasound transducer 20 provided in the ultrasound probe 2 to thereby generate an electric field. In this state, the ultrasound diagnostic apparatus 1 applies an ultrasound transmission pulse between the electrodes so as to vibrate a diaphragm to thereby transmit an ultrasound wave toward the subject. The ultrasound diagnostic apparatus 1 receives the ultrasound wave by detecting a vibration of the diaphragm caused by an ultrasound echo from the subject.

The DC bias circuit 6 and the transmission-reception separation circuit 7 are connected to the ultrasound probe 2. The transmission circuit 3, the reception circuit 8, and the discharge means 4 are connected to the transmission-reception separation circuit 7. The image-processing means 9 equipped with the display means 10 is connected to the reception circuit 8. The DC bias circuit 6, the transmission circuit 3, the discharge means 4, the reception circuit 8, and the image-processing means 9 are connected to the control means 5.

The transmission circuit 3 is a circuit for transmitting ultrasound transmission pulses to the transmission-reception separation circuit 7. The discharge means 4 is an apparatus for discharging any charge injected into an insulating portion of the ultrasound transducer 20 between the electrodes thereof. The DC bias circuit 6 is a circuit for controlling a DC bias applied to the ultrasound transducer 20 of the ultrasound probe 2. The transmission-reception separation circuit 7 is a circuit for separating ultrasound transmission pulses and ultrasound reception pulses from each other.

The reception circuit 8 receives ultrasound transmission pulses from the transmission-reception separation circuit 7. The image-processing means 9 is a computation apparatus which performs detection processing, etc. on the reception signals sent from the reception circuit 8 and reconstructs an ultrasound image. The display means 10 is a display apparatus, such as a monitor, which displays the ultrasound image sent from the image-processing means 9.

The control means 5 is an apparatus for controlling the state of the ultrasound diagnostic apparatus 1 and the respective apparatuses.

(1-2. Ultrasound Transducer 20)

Figure 2:
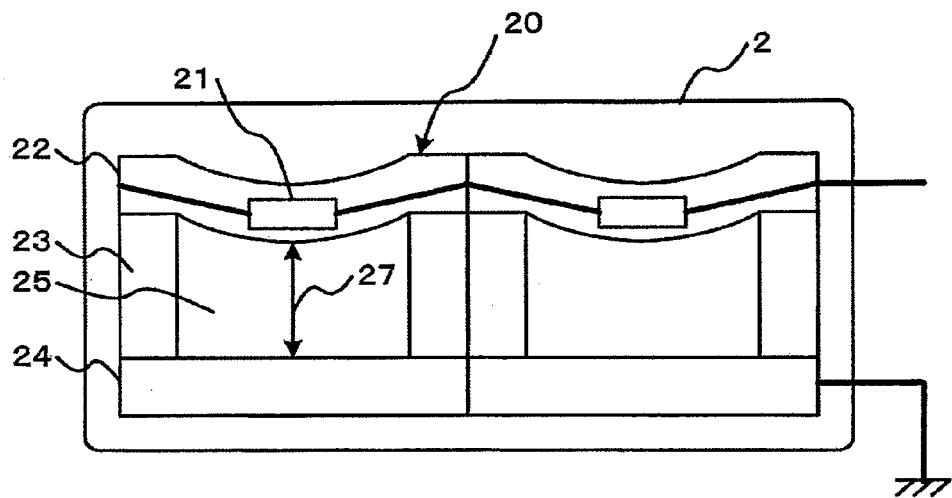
FIG. 2 View showing an ultrasound transducer 20 provided in an ultrasound probe 2.

FIG. 2 is a view showing the ultrasound transducer 20 provided in the ultrasound probe 2.

Notably, the ultrasound transducer 20 shown in FIG. 2 is a cMUT (Capacitive Micro-machined Ultrasound Transducer).

The ultrasound transducer 20 is composed of an upper electrode 21; a diaphragm 22 formed of a deformable insulating material; a rim 23 formed of an insulating material such as silicon nitride ($Si_3N_4$) and supporting the periphery of the diaphragm 22; a lower electrode 24; and a sacrificial layer 25, which is a vacuum gap layer formed between the upper electrode 21 and the lower electrode 24. The gap width 27 of the sacrificial layer 25 changes in accordance with a DC bias applied between the electrodes and vibration of the diaphragm 22. Notably, the "insulating portion" will be described as including the diaphragm 22 and the rim 23 between the upper electrode 21 and the lower electrode 24.

The ultrasound transducer 20 is a transducer whose ultrasound-wave transmission-reception sensitivity changes in accordance with a bias voltage superposed on a drive signal that drives the transducer. When ultrasound waves are transmitted and received by the ultrasound transducer 20, a predetermined bias is applied to the ultrasound transducer 20 so as to change the electromechanical coupling coefficient of the transducer to thereby adjust the transmission-reception sensitivity of the ultrasound transducer 20 to a predetermined value.

When a proper voltage signal is applied between the upper electrode 21 and the lower electrode 24, the ultrasound transducer 20 functions as a capacitive ultrasound transducer cell. An ultrasound echo signal is captured in the form of a change in kinetic energy of a sensor portion (the diaphragm 22 and the sacrificial layer 25), and a resultant change in current is detected, whereby a reception electric signal is obtained.

(1-3. Transmission Circuit 3)

Figure 3:
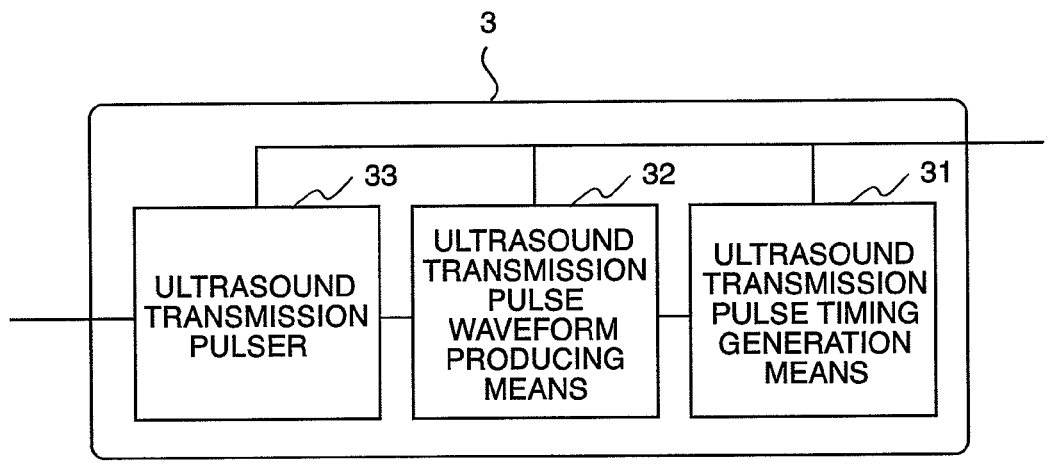
FIG. 3 Configurational diagram of a transmission circuit 3.

FIG. 3 is a configurational diagram of the transmission circuit 3.

The transmission circuit 3 is composed of ultrasound transmission pulse timing generation means 31 including a clock counter, etc.; ultrasound transmission pulse waveform producing means 32 including a selector, a memory, a memory control section, etc.; and ultrasound transmission pulser 33 including a clock divider, a buffer, a level shifter, a power driver, etc.

The control means 5 controls the transmission circuit 3; i.e., controls the waveform production by controlling the center frequency (e.g., 0.1 MHz to several tens MHz), wave number, envelope, etc., controls the generation timing by controlling the repeating frequency, delay for wave-transmission focusing, etc., and controls the output intensity by controlling the amplification factor, power source voltage, etc.

(1-4. Discharge circuit 4)

Figure 4:
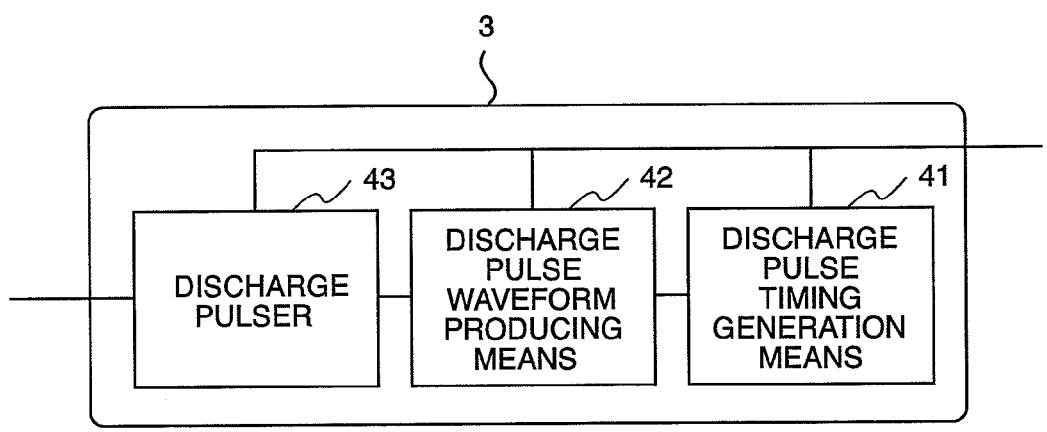
FIG. 4 Configurational diagram of a discharge circuit 4.

FIG. 4 is a configurational diagram of the discharge circuit 4.

The discharge circuit 4 is composed of discharge pulse timing generation means 41 including a clock counter, etc.; discharge pulse waveform producing means 42 including a selector, a memory, a memory control section, etc.; and a discharge pulser 43 including a clock divider, a buffer, a level shifter, a power driver, etc.

The control means 5 controls the discharge circuit 4; i.e., controls the waveform production by controlling the center frequency (e.g., several Hz to several tens kHz) and wave number, controls the generation timing by controlling the discharge trigger, the charge accumulation amount, etc., and controls the output intensity by controlling the amplification factor, power source voltage, etc.

The discharge pulse timing generation means 41 generates a discharge pulse generation timing signal with the clock division rate, the clock counter number, etc. being controlled by the control means 5.

The discharge pulse waveform producing means 42 selects a selector in accordance with the conditions, such as center frequency, wave number, envelope, etc. set by the control means 5. The memory control section controls the memory by performing read/write of waveform date and address setting in accordance with the condition selected by the selector, and produces a discharge pulse waveform when the discharge pulse timing generation means 41 generates the discharge pulse generation timing signal.

The discharge pulser 43 buffers, by means of a buffer, the discharge pulse waveform produced by the discharge pulse waveform producing means 42, and shifts the level of the discharge pulse waveform by means of a level shifter while amplifying the same. The power driver applies a discharge pulse between the electrodes of each ultrasound transducer 20 of the ultrasound probe 2.

Figure 5:
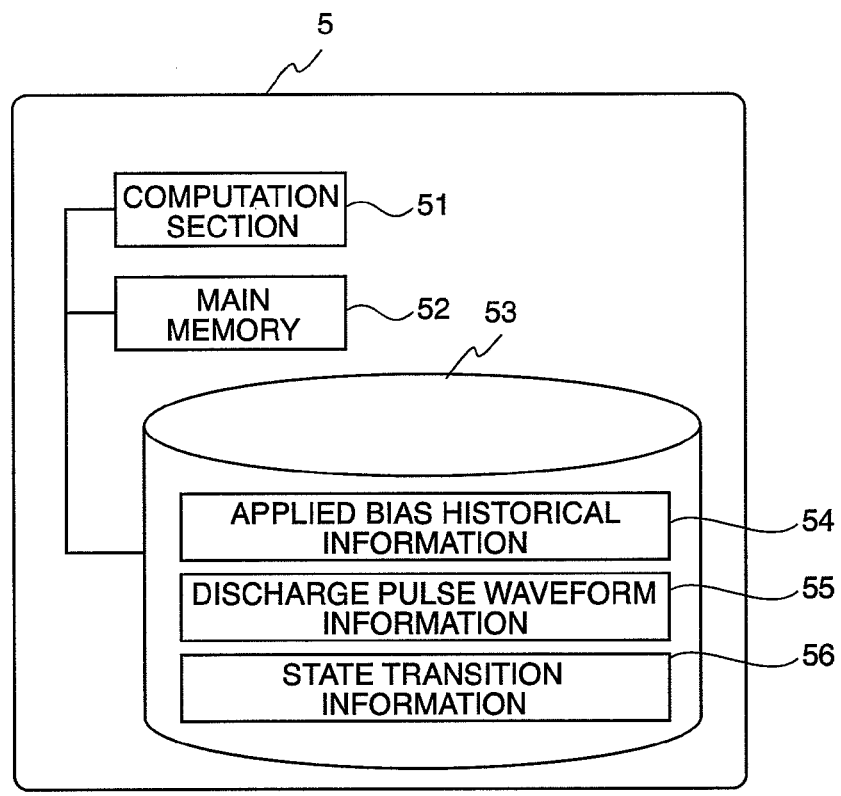
FIG. 5 Configurational diagram of control means 5.

FIG. 5 is a configrational diagram of the control means 5.

The control means 5 is composed of a computation section 51 such as a CPU, a main memory 52 such as RAM, and a storage section 53 such as a hard disk.

The storage section 53 holds applied bias historical information 54, discharge pulse waveform information 55, and state transition information 56.

The applied bias historical information 54 is a piece of information (application voltage, application time, etc.) regarding the history of application of a bias between the electrodes of the ultrasound transducer 20, and may assume the form of a Log file or the like.

The discharge pulse waveform information 55 is a piece of information regarding the discharge pulse waveform produced by the discharge means 4, and may assume the form of a Config file or the like.

The state transition information 56 is a piece of information regarding the state transition between an ordinary ultrasound-wave transmission-reception processing state and a discharge processing state in which the accumulated charge is discharged, and may assume the form of a State file, a flag, or the like.

The control means 5 retrieves the applied bias historical information 54, the discharge pulse waveform information 55, and the state transition information 56, and stores them in the main memory 52. The computation section 51 calculates, as information regarding the waveform of discharge pulses, the number of pulses and the application voltage and application time of each pulse (peak value $v_h$ ($t_h$), discharge time $t_h$, etc. of FIG. 10(b)) on the basis of the applied bias historical information 54 and in accordance with the conditions of the discharge pulse waveform information 55. On the basis of the state transition information 56 and in accordance with the conditions, the control means 5 effects switching between the ultrasound-wave transmission-reception processing state and the discharge processing state to thereby discharge any charge accumulated in the diaphragm 22 present between the electrodes of each ultrasound transducer 20 of the ultrasound probe 2.

(2. Charge Injection)

Next, injection of charge into an inter-electrode insulating portion will be described with reference to FIGS. and 7.

Figure 6:
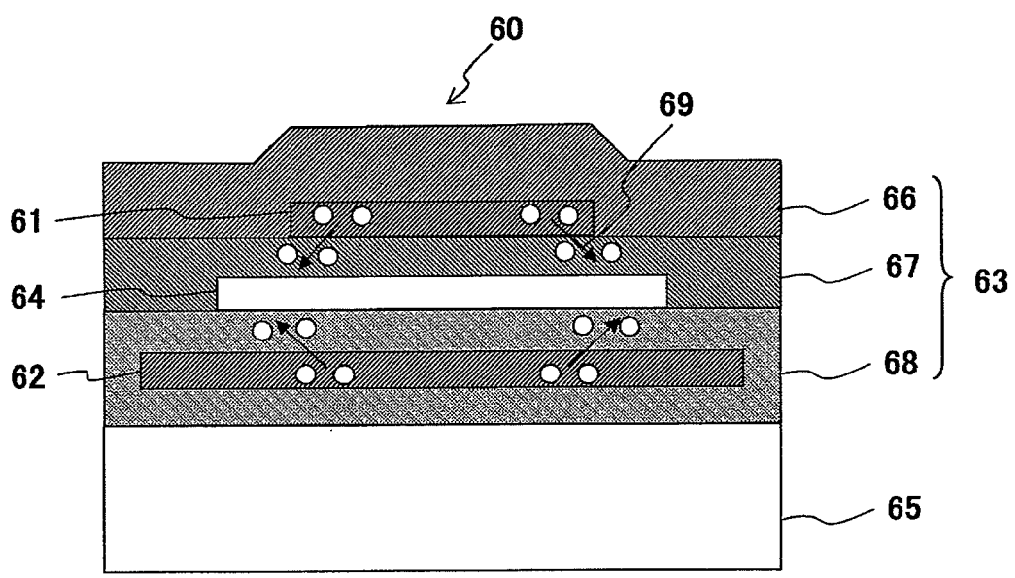
FIG. 6 Cross sectional view of an ultrasound transducer 60 showing one embodiment of the ultrasound transducer 20.

FIG. 6 is a cross sectional view of an ultrasound transducer 60 showing one embodiment of the ultrasound transducer 20.

The ultrasound transducer 60 is fabricated through micromachining by a semiconductor process. The ultrasound transducer 60 is composed of an upper electrode 61, a lower electrode 62, an insulating portion 63, a sacrificial layer 64, and a substrate 65. The insulating portion 63 is composed of a film 66, a frame 67, and a film 68. The insulating portion 63 is formed of an insulating material such as a silicon compound. The sacrificial layer 64 may be a vacuum chamber or a gas-charged chamber.

When a DC bias is applied between the upper electrode and the lower electrode 62, an electric field is generated therebetween. Although the insulating portion 63 is high in electrical resistance, a very small current flows through the insulating portion 63 upon generation of the electric field between the electrodes, with the resultant charge injection from the upper electrode 61 and the lower electrode 62 to the insulating portion 63. When application of the DC bias is interrupted, the charges in the upper electrode 61 and the lower electrode 62 become zero. However, the charge injected into the insulating portion 63 remains and accumulates. The accumulation amount of charge is proportional to the sum of product of the application voltage and application time of the DC bias.

A portion of the insulating portion 63 forms a diaphragm. If a charge is injected into the diaphragm portion of the insulating portion 63 and is accumulated therein, due to the influence of the inter-electrode field intensity, the transmission-reception sensitivity changes. Further, the accumulated charge causes a transmission-reception sensitivity drift, whereby a transmission-reception sensitivity distortion occurs.

Figure 7:
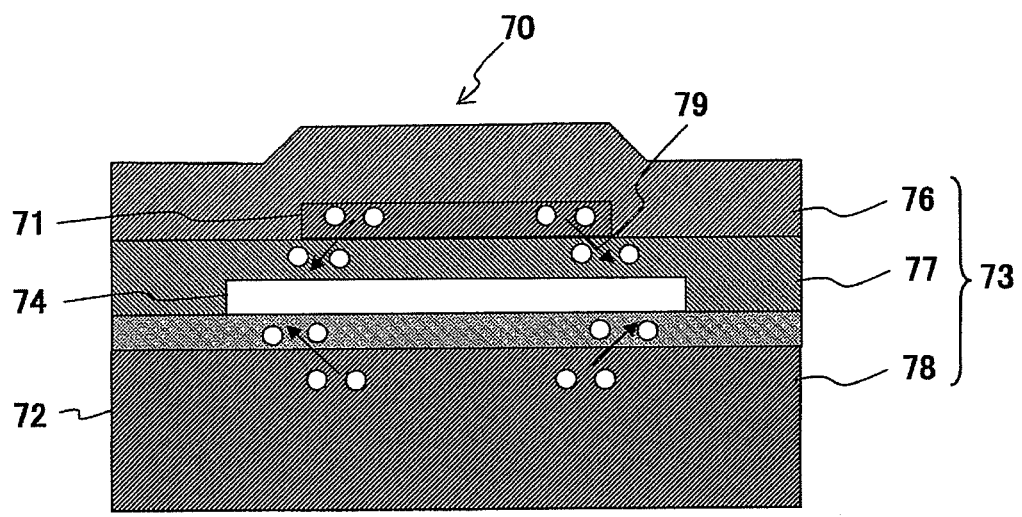
FIG. 7 Cross sectional view of an ultrasound transducer 70 showing another embodiment of the ultrasound transducer 20.

FIG. 7 is a cross sectional view of an ultrasound transducer 70 showing another embodiment of the ultrasound transducer 20.

The ultrasound transducer 70 is composed of an upper electrode 71, a lower electrode 72, an insulating portion 73, and a sacrificial layer 74. The insulating portion 73 is composed of a film 76, a frame 77, and a film 78. The upper electrode 71, the insulating portion 73, and the sacrificial layer 74 of FIG. 7 are similar to the upper electrode 61, the insulating portion 63, and the sacrificial layer 64 of FIG. 6. The lower electrode 72 of FIG. 7 corresponds to the substrate of FIG. 6, which is used as a lower electrode in FIG. 7.

In the ultrasound transducer 70 of FIG. 7 as well, like the ultrasound transducer 60 of FIG. 6, there occurs charge injection 79 from the upper electrode 71 and the lower electrode 72 to the insulating portion 73.

(3. Transmission-Reception Sensitivity Drift)

Next, transmission-reception sensitivity drift will be described with reference to FIG. 8.

Figure 8:
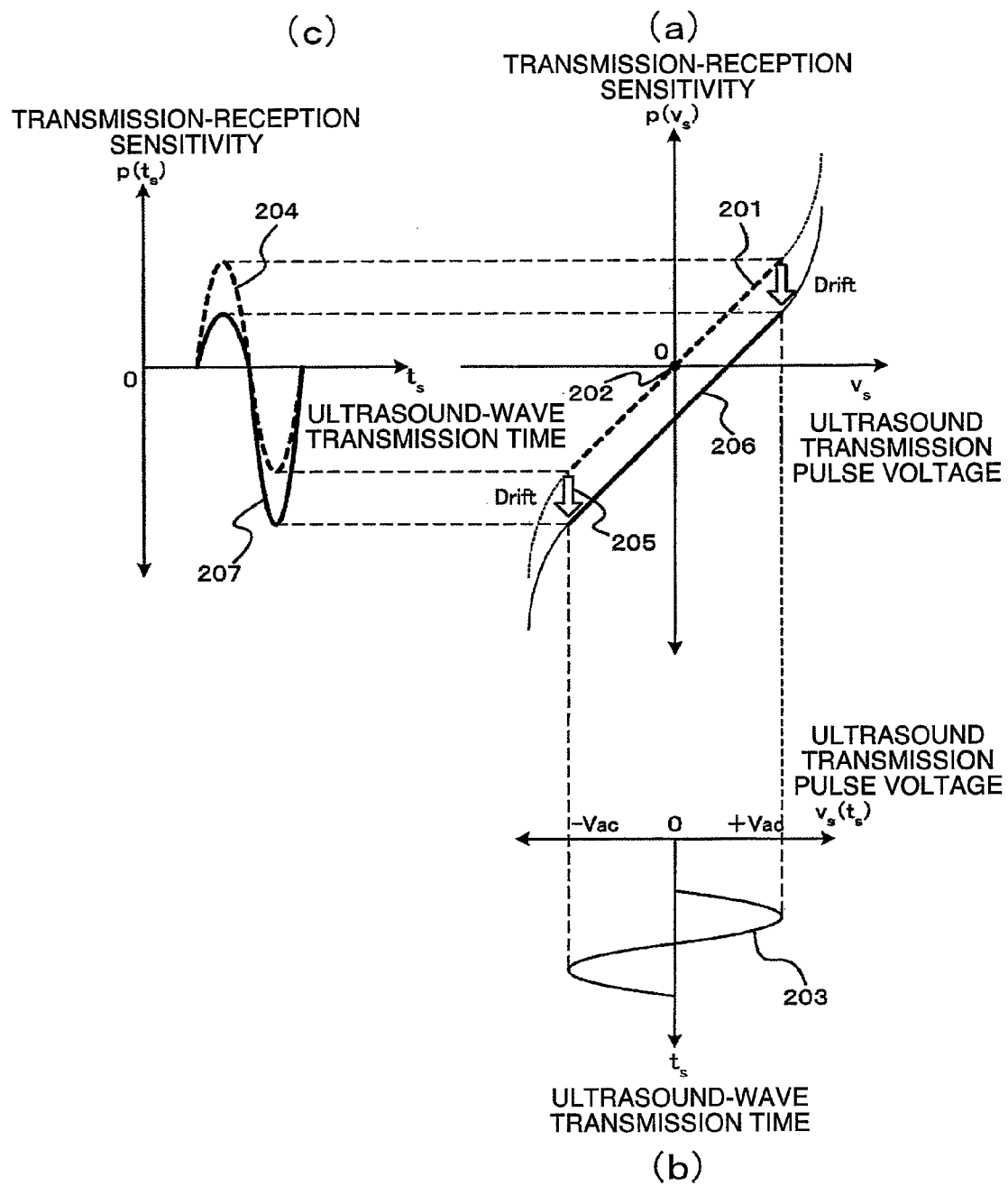
FIG. 8 Graphs showing the relation among ultrasound transmission pulse voltage, transmission-reception sensitivity, etc.

FIG. 8 is a set of graphs showing the relation among ultrasound transmission pulse voltage, transmission-reception sensitivity, etc.

FIG. 8(a) is a graph showing the relation between ultrasound transmission pulse voltage and transmission-reception sensitivity. The horizontal axis represents ultrasound transmission pulse voltage $v_s$, and the vertical axis represents transmission-reception sensitivity $p(v_s)$.

FIG. 8(b) is a graph showing the relation between ultrasound transmission pulse voltage and time. The horizontal axis represents ultrasound transmission pulse voltage $v_s$ ($t_s$), and the vertical axis represents ultrasound-wave transmission time $t_s$.

FIG. 8(c) is a graph showing the relation between ultrasound-wave transmission time and transmission-reception sensitivity. The horizontal axis represents ultrasound-wave transmission time $t_s$, and the vertical axis represents transmission-reception sensitivity $p(t_s)$.

A line 201 shows the relation between ultrasound transmission pulse voltage and transmission-reception sensitivity for the case where a DC bias is applied between the electrodes of the ultrasound transducer 20 for a relatively short time. The line 201 is a straight line passing through the origin 202. When an ultrasound transmission pulse voltage $v_s$ (AC pulse) having the same amplitude in the positive and negative polarities as indicated by a curve 203 is applied, the transmission-reception sensitivity $p(t_s)$ has neither deviation nor distortion in the positive and negative polarities as indicated by a curve 204.

Meanwhile, in the case where a DC bias is applied between the electrodes of the ultrasound transducer 20 for a long time, if a charge is injected into the diaphragm 22 of the ultrasound transducer 20, a deviation of the transmission-reception sensitivity in the positive and negative polarities; i.e., a transmission-reception sensitivity drift 205, is produced. When such transmission-reception sensitivity drift 205 is produced, the relation between ultrasound transmission pulse voltage and transmission-reception sensitivity moves as indicated by a line 206. This line 206 does not pass through the origin 202. When an ultrasound transmission pulse voltage $v_s$ (AC pulse) having the same amplitude in the positive and negative polarities as indicated by the curve 203 is applied, the transmission-reception sensitivity $p(t_s)$ has deviation and distortion in the positive and negative polarities as indicated by a curve 207. This transmission-reception sensitivity distortion causes an increase in harmonic components.

(4. Discharge Processing of the Ultrasound Diagnostic Apparatus 1)

Next, the discharge processing of the ultrasound diagnostic apparatus 1 will be described with reference to FIGS. 9 to 11.

The ultrasound diagnostic apparatus 1 of the present invention is characterized in that the charge accumulated between the electrodes of the ultrasound transducer 20 is discharged within a short time by making use of a collapse phenomenon and a snapback phenomenon.

(4-1. Collapse Phenomenon and Snapback Phenomenon)

If the magnitude of the DC bias applied between the electrodes of the ultrasound transducer 20 falls within a predetermined range, because of balance between an elastic force of the diaphragm 22 and a Coulomb force generated through application of the DC bias, the gap width 27 of the sacrificial layer 25 becomes a predetermined width, and a balanced state is created.

Meanwhile, when the DC bias applied between the electrodes of the ultrasound transducer 20 increases, the Coulomb force increases, and balance is attained when the gap width 27 of the sacrificial layer 25 has decreased.

Further, when the DC bias applied between the electrodes of the ultrasound transducer 20 increases beyond the predetermined range, the elastic force of the diaphragm 22 becomes unable to support the Coulomb force generated through application of the DC bias, and an imbalanced state is created. As a result, the gap width 27 of the sacrificial layer 25 quickly decreases to zero. This phenomenon and state are called a "collapse phenomenon" and a "collapse state," respectively. A threshold value of the application voltage at which the collapse state is created is called a "collapse voltage."

In a state in which the collapse phenomenon has not yet occurred, injection of charge into the insulating portion occurs in accordance with the ratio between the impedance of the diaphragm 22 and the rim 23 and the DC bias application voltage.

Meanwhile, in the collapse state, injection of charge occurs in accordance with the ratio between the impedance of the diaphragm 22 only and the DC bias application voltage. In the collapse state, since the impedance decreases quickly, the charge injection speed increases.

When the DC bias application voltage is reduced in the collapse state, the Coulomb force decreases. As a result, a phenomenon which is inverse of the collapse phenomenon occurs, so that the gap width of the sacrificial layer 25 quickly changes from zero to the predetermined width. This phenomenon is called a "snapback phenomenon." A threshold value of the application voltage at which the snapback phenomenon occurs is called a "snapback voltage."

That is, when the collapse phenomenon occurs, the elastic force of the diaphragm 22 and the Coulomb force become unbalance. However, the diaphragm 22 does not lose its elastic property. Accordingly, when the snapback phenomenon occurs, the balance between the elastic force of the diaphragm 22 and the Coulomb force is restored.

After occurrence of the snapback phenomenon, injection of charge occurs in accordance with the ratio of the DC bias application voltage to the impedance of the diaphragm 22 and the rim 23.

(4-2. Details of the Discharge Processing)

Figure 9:
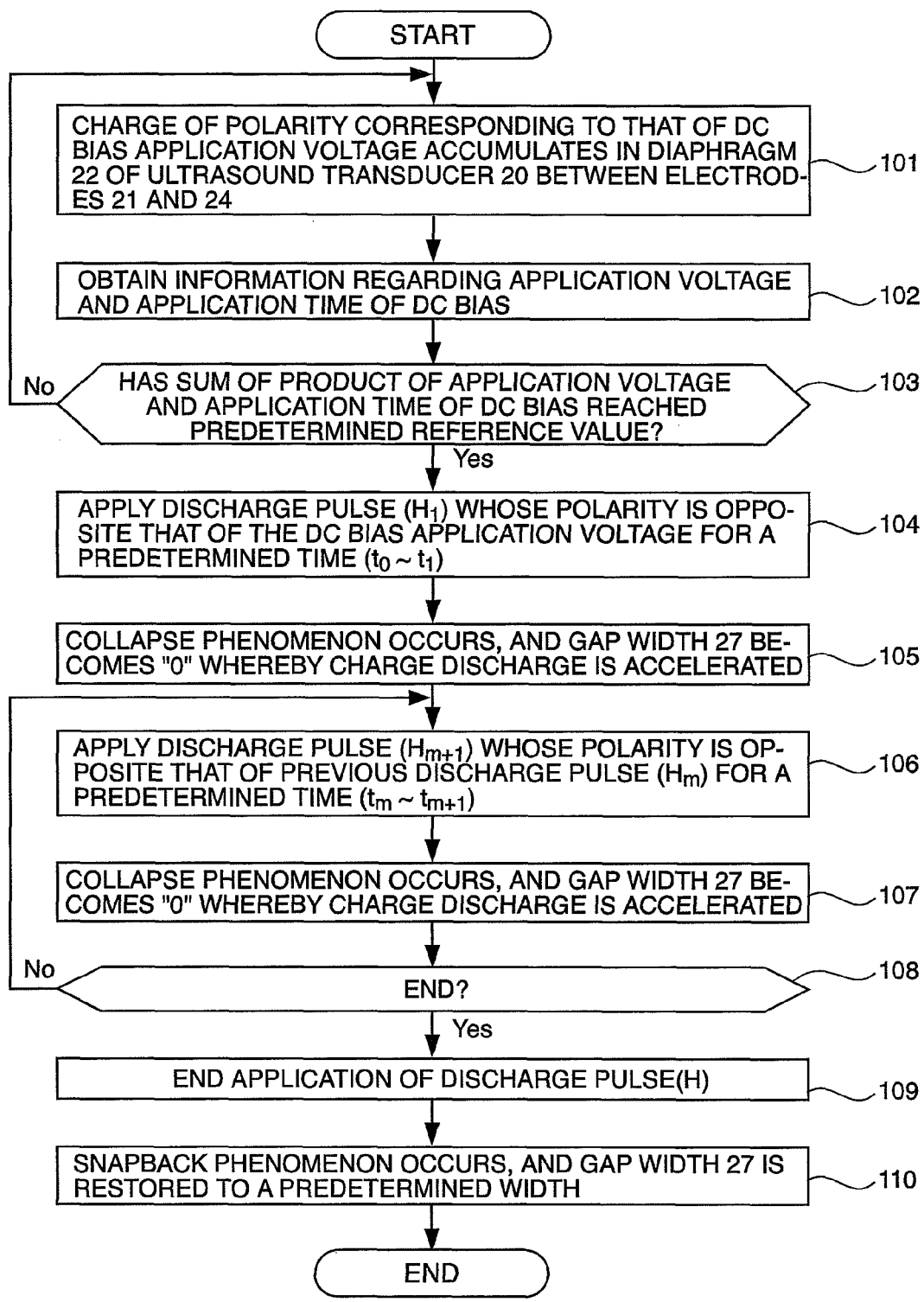
FIG. 9 Flowchart showing discharge processing.

FIG. 9 is a flowchart showing the discharge processing.

Figure 10:
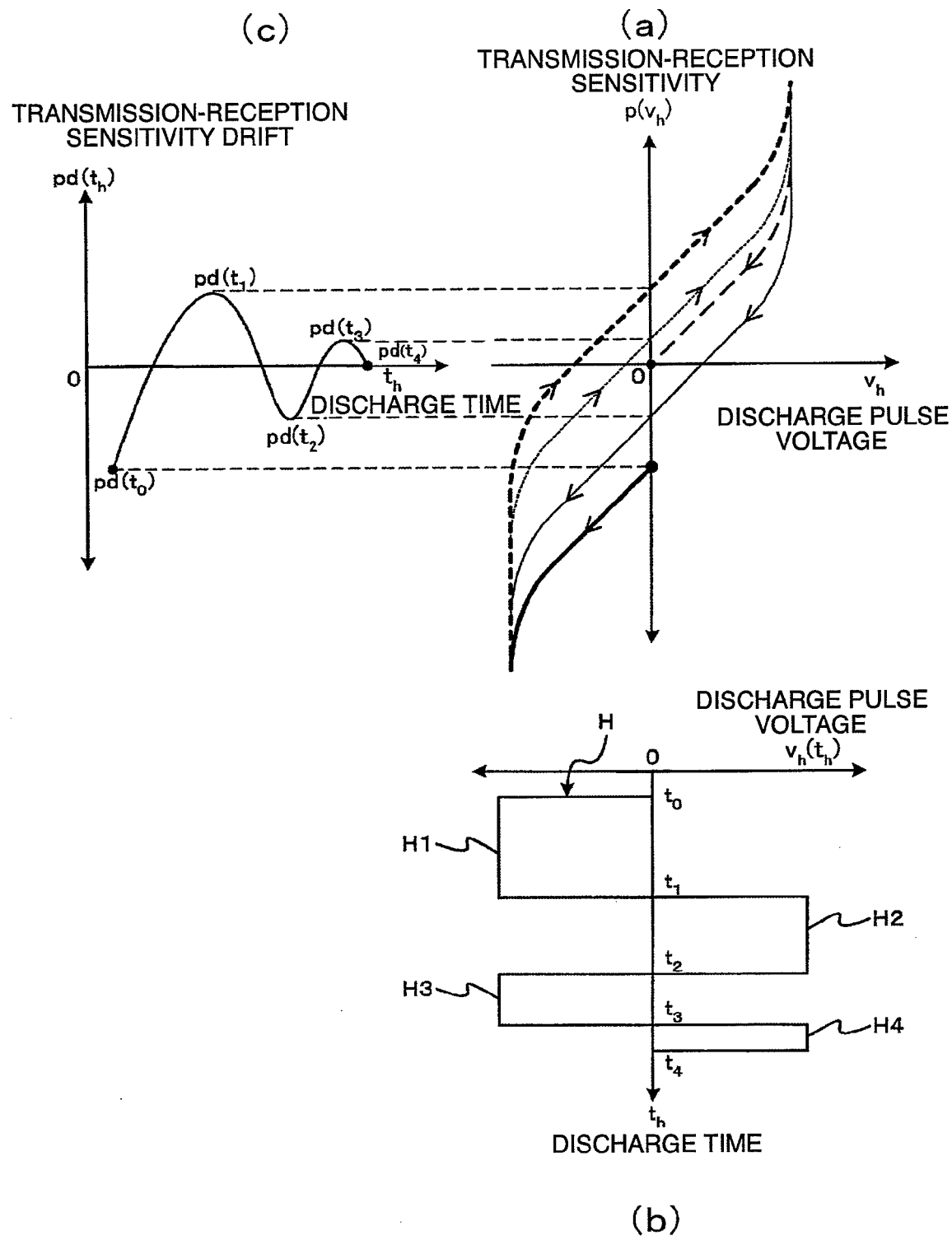
FIG. 10 Graphs showing the relation among discharge pulse voltage, transmission-reception sensitivity, transmission-reception sensitivity drift, etc.

FIG. 10 is a set of graphs showing the relation among discharge pulse voltage, transmission-reception sensitivity, transmission-reception sensitivity drift, etc.

FIG. 10(*a*) is a graph showing the relation between discharge pulse voltage and transmission-reception sensitivity. The horizontal axis represents discharge pulse voltage $v_h$, and the vertical axis represents transmission-reception sensitivity $p(v_h)$.

FIG. 10(*b*) is a graph showing the relation between discharge pulse voltage and time. The horizontal axis represents discharge pulse voltage $v_h(t_h)$, and the vertical axis represents discharge time $t_h$.

FIG. 10(*c*) is a graph showing the relation between discharge time and transmission-reception sensitivity drift. The horizontal axis represents discharge time $t_h$, and the vertical axis represents transmission-reception sensitivity drift $pd(t_h)$.

When the ultrasound diagnostic apparatus 1 continues ultrasound-wave transmission processing, a charge whose polarity corresponds to that of the DC bias application voltage accumulates in the insulating portion between the electrodes 21 and 24 of the ultrasound transducer 20 (step 101).

The control means 5 obtains, through measurement, information regarding the application voltage and application time of the DC bias, and records them as the applied bias historical information 54 (step 102). The control means 5 determines whether or not the sum of product of the application voltage and application time of the DC bias has reached a predetermined reference value. When the sum has reached the predetermined reference value (Yes in step 103), the control means 5 proceeds to the discharge processing in step 104 and steps subsequent thereto.

In order to discharge the injected charge, the discharge means 4 applies between the electrodes of the ultrasound transducer 20 a discharge pulse ($H_1$) whose polarity is opposite that of the ordinary DC bias application voltage, for a predetermined time ($t_0$ to $t_1$) (step 104). Notably, the predetermined time ($t_0$ to $t_1$) is desirably set such that a reverse charge is injected slightly, in consideration of variations of conditions.

The peak value ($v_h(t_h)$) of the discharge pulse ($H_1$) is equal to or greater than the collapse voltage, so that the collapse phenomenon occurs. The gap width 27 of the sacrificial layer 25 becomes zero, and the discharge of the charge is accelerated (step 105).

Next, in order to discharge the remaining reverse charge, the discharge means 4 applies between the electrodes of the ultrasound transducer 20 a discharge pulse ($H_2$) whose polarity is opposite that of the previous discharge pulse ($H_1$), for a predetermined time ($t_1$ to $t_2$) (step 106). Notably, the predetermined time ($t_1$ to $t_2$) is desirably set such that a reverse charge is injected slightly, in consideration of variations of conditions. Further, the predetermined time ($t_1$ to $t_2$) desirably satisfies the relation the predetermined time ($t_0$ to $t_1$) >the predetermined time ($t_1$ to $t_2$).

The peak value ($v_h(t_h)$) of the discharge pulse ($H_2$) is equal to or greater than the collapse voltage, so that the collapse phenomenon occurs. The gap width 27 of the sacrificial layer 25 becomes zero, and the discharge of the charge is accelerated (step 107).

When it is determined that the processing of steps 104 and 105 has been repeated a predetermined number of times (step 108), the discharge means 4 ends the application of the discharge pulse (H) (step 109). Preferably, the discharge means 4 gradually shortens the application time such that the predetermined time ($t_0$ to $t_1$) >the predetermined time ($t_1$ to $t_2$)> . . . >the predetermined time ($t_{m-1}$ to $t_m$)>the predetermined time ($t_m$ to $t_{m+1}$).

When the voltage applied between the electrodes of the ultrasound transducer 20 becomes equal to or lower than the collapse voltage, the snapback phenomenon occurs, and the gap width 27 of the sacrificial layer 25 is restored to the predetermined width (step 110). The transmission-reception sensitivity drift ($pd(t_h)$) generally converges to "0."

FIG. 10 shows an example in which the discharge pulse (H) is applied four times, while its polarity is inverted each time.

When the discharge means 4 applies the discharge pulse ($H_1$) between the electrodes of the ultrasound transducer 20, the transmission-reception sensitivity drift $pd(t_0)$ changes to a transmission-reception sensitivity drift $pd(t_1)$. Similarly, when the discharge means 4 successively applies the discharge pulse ($H_2$), the discharge pulse ($H_3$), and the discharge pulse ($H_4$) between the electrodes of the ultrasound transducer 20, the transmission-reception sensitivity drift changes in such a manner that $pd(t_2) \rightarrow pd(t_3) \rightarrow pd(t_4)$. The transmission-reception sensitivity drift $pd(t_4)$ generally converges to "0."

Notably, the number of times the discharge pulse is applied with its polarity reversed each time is at least one. The ultrasound probe 2 is composed of a large number of ultrasound transducers 20. Since the characteristics vary among the ultrasound transducers 20, the transmission-reception sensitivity drifts of all the ultrasound transducers 20 cannot be made zero simultaneously through a single-time application of a reverse-polarity discharge pulse. Although the transmission-reception sensitivity drift can be improved to some degree through the single-time application of a reverse-polarity discharge pulse, it is desired to apply the discharge pulse a plurality of times with its polarity reversed each time to thereby converge the transmission-reception sensitivity drift to zero as shown in FIGS. 9 and 10.

The discharge processing shown in steps 104 to 109 of FIG. 9 and FIG. 10 completes within a short time not longer than 1 sec. Accordingly, the discharge processing is desirably performed when the power is turned on or off, or when the transmission and reception of ultrasound waves is stopped (at the time of freeze).

As described above, the ultrasound diagnostic apparatus 1 of the first embodiment causes the discharge means 4 to apply a discharge pulse (having a peak value equal to or greater than the collapse voltage) between the electrodes of the ultrasound transducer 20 a plurality of times while inverting the polarity of the discharge pulse alternately, to thereby accelerate discharge of the charge accumulated in the diaphragm 22 of the ultrasound transducer 20, so that the transmission-reception sensitivity offset can be caused to quickly approach zero. The charge is discharged instantaneously. That is, it is possible to quickly calibrate the transmission-reception sensitivity drift stemming from time-course accumulation of charge flowing into the insulating portion between the electrodes upon application of the DC bias thereto.

(4-3. Monitoring of Charge Accumulation)

Figures 11, 12:
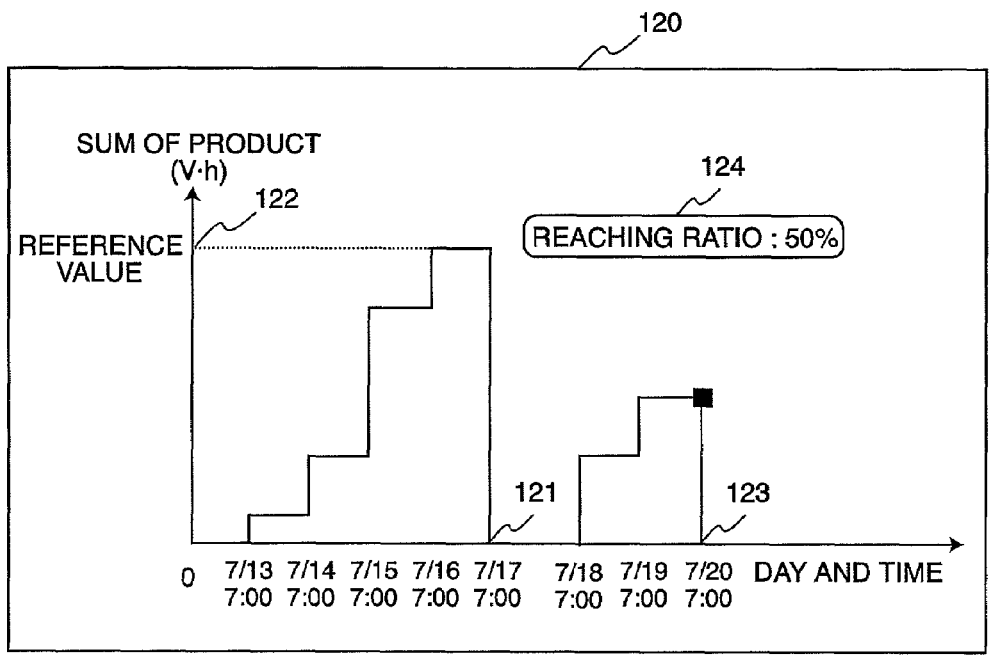
FIG. 11 Illustration showing a table 110, which is one embodiment of applied bias historical information 54 and state transition information 56.
FIG. 12 Illustration showing one embodiment of a screen 120 of display means 10.

FIG. 11 is an illustration showing a table 110, which is one embodiment of the applied bias historical information 54 and the state transition information 56.

Various items; i.e., date 111, time 112, application time 113, application voltage 114, sum of product 115, and state 116, are recorded in the table 110. The date 111, the time 112, the application time 113, the application voltage 114, and the sum of product 115 correspond to the applied bias historical information 54 of FIG. 5. The state 116 corresponds to the state transition information 56 of FIG. 5.

The date 111 and the time 112 show the date and time of each application of a DC bias. The application time 113 shows the application time of the DC bias; for example, "2 h." The application voltage 114 shows the application voltage of the DC bias; for example, "100 V." The sum of product 115 shows the sum of product of the application voltage and application time of the DC bias after the previous discharge processing; for example, "200 V·h." The state 116 shows the charge accumulation state or the execution of the discharge processing. For example, the reaching ratio of the sum of product 115 in relation to a predetermined reference value (e.g., "30000 V·h") is recorded as the state 116.

In the processing of step 102 of FIG. 9, the control means 5 records the date 111, the time 112, the application time 113, the application voltage 114, and the sum of product 115 of the table 110. In the processing of step 103 of FIG. 9, the control means 5 determines whether or not the sum of product 115 of the table 110 has reached the predetermined reference value. When the sum has reached the predetermined reference value (Yes in step 103), the control means 5 performs the discharge processing in step 104 and subsequent steps of FIG. 9. The control means 5 calculates the execution timing of the discharge processing and the waveform information (the pulse number and the application voltage and application time of each pulse) of discharge pulses (H) shown in FIG. 10(b) by reference to the table 110, and applies the discharge pulses between the electrodes.

Thus, the start timing of the discharge processing can be properly determined.

(4-4. Display of DC Bias Application History and State)

FIG. 12 is an illustration showing one embodiment of the screen 120 of the display means 10.

The display means 10 displays the charge accumulation state in the form of a graph on the basis of the applied bias historical information 54 and the state transition information 56.

On the screen 120, the vertical axis indicates the sum of product of the application voltage and application time of the DC bias, and the horizontal axis indicates date and time. At a time point 121, the sum of product of the application voltage and application time of the DC bias reaches a predetermined reference value 122, and therefore, the discharge processing is performed. Further, the reaching ratio 124 of the sum of product, as calculated at the present time point 123 in relation to the predetermined reference value 122, may be displayed. Further, necessity of the discharge processing may be displayed.

The screen 120 allows grasping of the charge accumulation amount, and the necessity and timing of the discharge processing. Notably, in the present embodiment, the control means 5 determines the timing at which the discharge processing is to be started, and automatically executes the discharge processing. However, a discharge switch or the like may be provided on the apparatus main body so as to manually execute the discharge processing. In this case, desirably, the manual execution of the discharge processing is effected on the basis of the above-described reaching ratio and the necessity of the discharge processing displayed by the display means 10.

(5. Second Embodiment)

Next, an ultrasound diagnostic apparatus 1a according to a second embodiment will be described with reference to FIG. 13.

Figure 13:
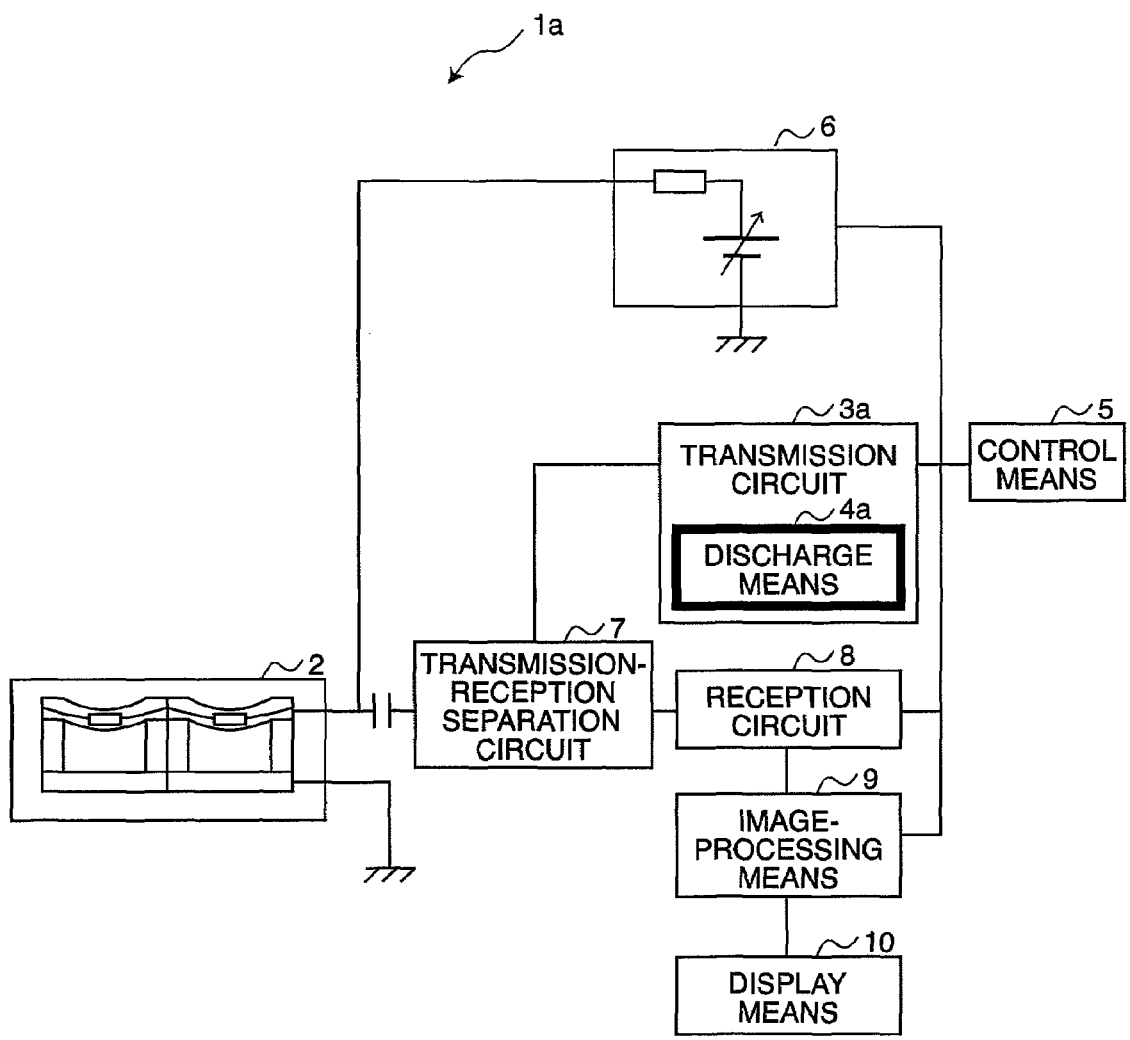
FIG. 13 Schematic configurational diagram of an ultrasound diagnostic apparatus 1a (second embodiment).

FIG. 13 is a schematic configurational diagram of the ultrasound diagnostic apparatus 1a.

In the ultrasound diagnostic apparatus 1 of the first embodiment, the discharge means 4 is configured independently. In contrast, in the ultrasound diagnostic apparatus 1a of the second embodiment, a transmission circuit 3a and discharge means 4a share a portion or the entirely of pulse timing generation means, pulse waveform producing means, and a pulser. For example, the transmission circuit 3a may be configured to contain the discharge means 4 therein.

In the second embodiment, as in the first embodiment, the ultrasound diagnostic apparatus 1a causes the discharge means 4a to apply a discharge pulse (having a peak value equal to or greater than the collapse voltage) between the electrodes of the ultrasound transducer 20 a plurality of time while inverting the polarity of the discharge pulse each time, to thereby accelerate discharge of the charge accumulated in the diaphragm 22 of the ultrasound transducer 20, so that the transmission-reception sensitivity offset can be caused to quickly approach zero.

Further, in the second embodiment, the transmission circuit 3a and the discharge means 4a share a portion of constituent elements. Therefore, the configuration of the apparatus can be simplified.

(6. Third Embodiment)

Next, an ultrasound diagnostic apparatus 1b according to a third embodiment will be described with reference to FIG. 14.

Figure 14:
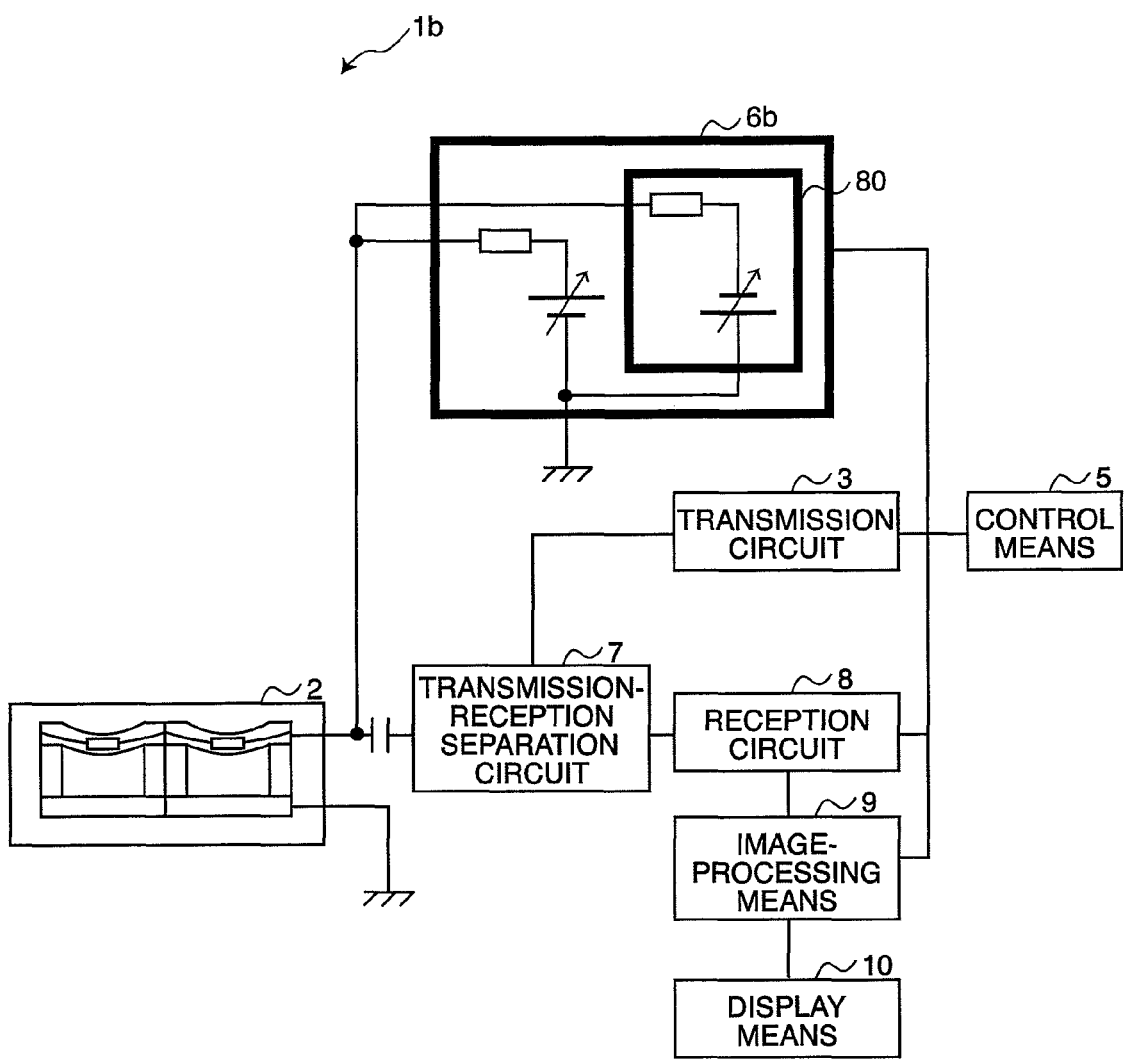
FIG. 14 Schematic configurational diagram of an ultrasound diagnostic apparatus 1b (third embodiment).

FIG. 14 is a schematic configurational diagram of the ultrasound diagnostic apparatus 1b.

In the ultrasound diagnostic apparatus 1 of the first embodiment, the discharge means 4 is configured independently. In contrast, in the ultrasound diagnostic apparatus 1b of the third embodiment, discharge means 80 is incorporated into a DC bias circuit 6b.

The DC bias circuit 6b containing the discharge means 80 changes the DC bias applied between the electrodes of the ultrasound transducer 20 to thereby accelerate discharge of the charge accumulated in the diaphragm 22 of the ultrasound transducer 20.

In the ultrasound diagnostic apparatus 1b, in place of discharge pulses equal to or higher than the collapse voltage, which is employed in the first and second embodiments, a reverse-polarity DC bias equal to or less than the collapse voltage is applied by reference to the applied bias historical information 54 of the storage section 53, whereby the charge injected into the diaphragm 22 of the ultrasound transducer 20 can be discharged.

In the third embodiment, a reverse-polarity DC bias which is equal to or less than the collapse voltage is applied by means of the DC bias circuit 6b containing the discharge means 80, whereby discharge of the charge accumulated in the diaphragm 22 of the ultrasound transducer 20 can be accelerated, and the transmission-reception sensitivity offset can be caused to quickly approach zero.

Notably, when a DC bias equal to or less than the collapse voltage is applied, the discharge processing continues for several hours. Accordingly, it is desired to provide, on an operation device such as a keyboard or a monitor, a switch for starting the discharge processing, and to provide reporting means for providing a display, warning, or the like which indicates that the discharge processing is being executed.

Further, in the third embodiment, pulse timing generation means, pulse waveform producing means, and a pulser are not required for the discharge processing. Therefore, the configuration of the apparatus can be simplified.

Notably, it is theoretically possible to perform the processing of discharging the accumulated charge through application of a DC bias equal to or higher than the collapse voltage. However, in a case where a reverse-polarity DC bias equal to or higher than the collapse voltage is applied, there is a possibility that the charge injection proceeds instead and the transmission-reception sensitivity drift increases. Therefore, discharge through gradual application of a reverse-polarity DC bias equal to or less than the collapse voltage is simple and reliable, and is preferable from the viewpoint of safety.

(7. Fourth Embodiment)

Next, an ultrasound diagnostic apparatus 1c according to a fourth embodiment will be described with reference to FIG. 15.

Figure 15:
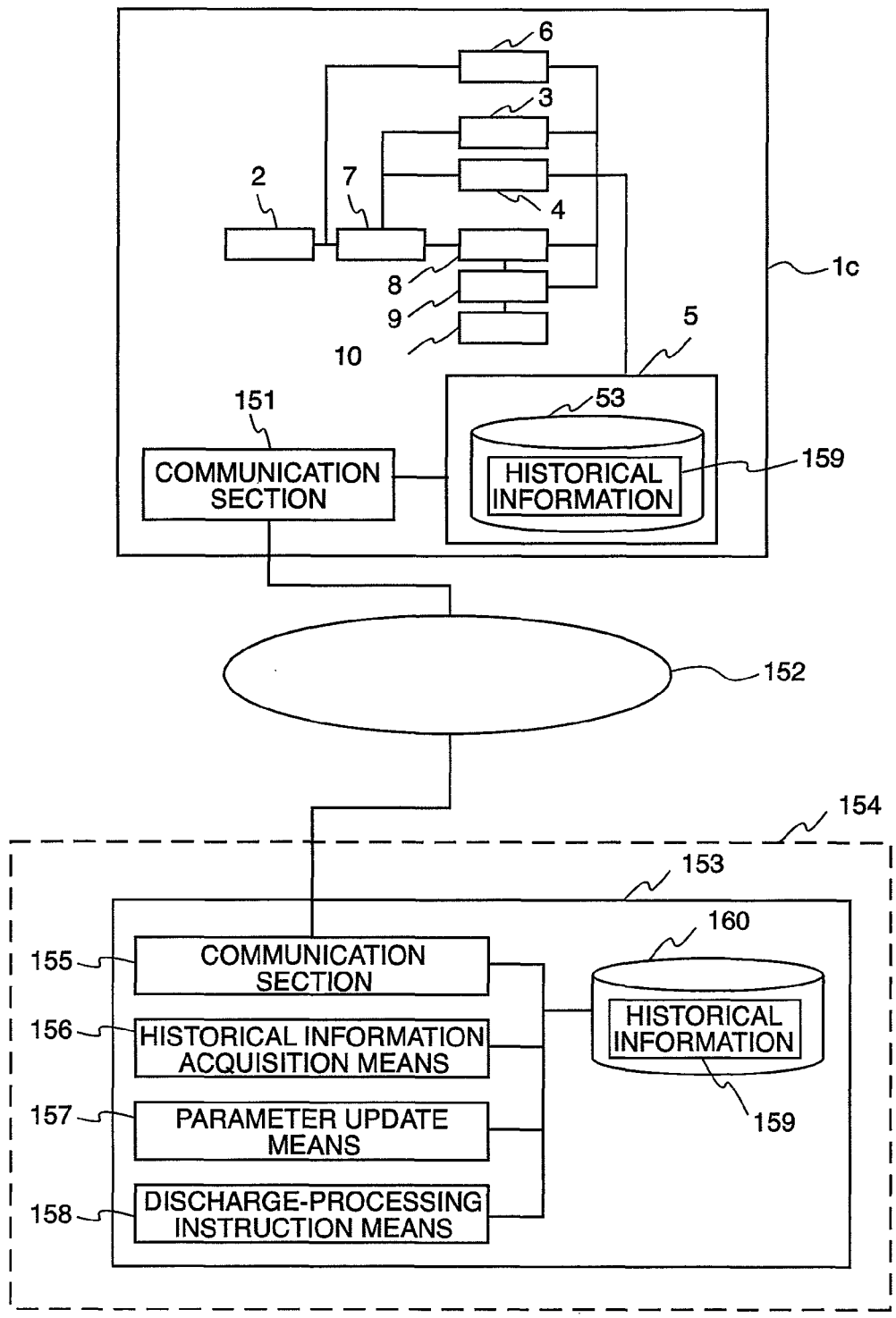
FIG. 15 Schematic configurational diagram of an ultrasound diagnostic apparatus 1c and an external control apparatus 153 (fourth embodiment).

FIG. 15 is a schematic configurational diagram of the ultrasound diagnostic apparatus 1c and an external control apparatus 153.

In the first embodiment, the ultrasound diagnostic apparatus 1 itself calculates the timing for the discharge processing and the discharge pulse waveform information so as to execute the discharge processing. In contrast, in the fourth embodiment, the external control apparatus 153 calculates the timing for the discharge processing and the discharge pulse waveform information.

The ultrasound diagnostic apparatus 1c is connected via a network 152 to the external control apparatus 153 belonging to a remote maintenance center 154. The ultrasound diagnostic apparatus 1c is similar to the ultrasound diagnostic apparatus 1 of FIG. 1. The external control apparatus 153 includes historical information acquisition means 156, parameter update means 157, discharge-processing instruction means 158, and a storage section 160. The external control apparatus 153 is a terminal apparatus such as a personal computer. The network 152 is a radio communication line such as personal handy-phone system, or a network line such as the internet. The ultrasound diagnostic apparatus 1c and the external control apparatus 153 include a communication section 151 and a communication section 155, respectively, and can exchange information via the communication section 151, the network 152, and the communication section 155.

The historical information 159 is transmitted and received between the ultrasound diagnostic apparatus 1c and the external control apparatus 153 at constant intervals or intermittently in accordance with the state of use. The historical information 159 includes history regarding application of a DC bias between the electrodes and history regarding application of discharge pulses between the electrodes. The transmission and reception of the historical information 159 is effected in such a manner that the ultrasound diagnostic apparatus 1c actively transmits the historical information 159 to the external control apparatus 153 or in such a manner that the external control apparatus 153 actively acquires the historical information 159 from the ultrasound diagnostic apparatus 1c.

The external control apparatus 153 acquires the historical information 159 held in the storage section 53 of the ultrasound diagnostic apparatus 1c by means of the historical information acquisition means 156, and stores the information in the storage section 160. The external control apparatus 153 checks the charging-discharging state of the charge in the insulating portion of the ultrasound diagnostic apparatus 1c by reference to the historical information 159.

Also, the external control apparatus 153 causes the parameter update means 157 to check various pieces of information such as parameters for determining the peak value of the discharge pulse waveform, the predetermined time, and the number of times, etc., and parameters for determining the condition of state transition. Further, when necessary, the external control apparatus 153 causes the parameter update means 157 to transmit update values of these parameters to the ultrasound diagnostic apparatus 1c for update.

Moreover, the external control apparatus 153 causes the discharge-processing instruction means 158 to instruct the ultrasound diagnostic apparatus 1c to execute the discharge processing.

On the basis of discharge processing instruction and the parameters associated with the discharge processing and transmitted from the external control apparatus 153, the ultrasound diagnostic apparatus 1c updates these parameters and executes the discharge processing. The ultrasound diagnostic apparatus 1c transmits to the external control apparatus 153 the results of the update of the parameters and the results of the execution of the discharge processing.

As described above, in the fourth embodiment, the external control apparatus 153 can control update of the parameters associated with the discharge processing in the ultrasound diagnostic apparatus 1c and the timing of the discharge processing. Further, when a plurality of ultrasound diagnostic apparatus 1c are connected to the network 152, it becomes possible to enable the single external control apparatus 153 to centrally manage the discharge processing in the plurality of ultrasound diagnostic apparatus 1c.

(8. Others)

In the above-described embodiment, the charge injected into a diaphragm of an ultrasound transducer due to application of a DC bias over a long time is quickly discharged by utilizing the collapse phenomenon and the snapback phenomenon. However, the charge within the diaphragm can be discharged by a shunt switch, such as a mechanical relay, which is formed in the ultrasound transducer by utilizing an MEMS (Micro Electro Mechanical System). In this case, the charge can be discharged by controlling the open/close state of the shunt switch.

Further, the control means 5 may be configured to monitor the state transition between the ultrasound-wave transmission-reception processing state and the discharge processing state, and report the processing state to an operator of the ultrasound diagnostic apparatus 1. For example, the control means 5 may report the fact of the discharge processing currently being executed to the operator of the ultrasound diagnostic apparatus 1 by providing an alert display on the display means 10, sound information, or the like.

Preferred embodiments of the ultrasound diagnostic apparatus according to the present invention have been described with reference to the accompanying drawings. However, the present invention is not limited to the above-described embodiments. It is clear that a person with ordinary skill in the art can easily conceive various modifications and changes within the technical idea disclosed herein, and it is contemplated that such modifications and changes naturally fall within the technical scope of the present invention.

The invention claimed is:

1. An ultrasound diagnostic apparatus comprising:
   an ultrasound probe equipped with an ultrasound transducer including a pair of electrodes and an insulating portion and a sacrificial layer provided between the electrodes;
   a DC-bias applier configured to apply a DC bias between the electrodes;
   a transmitter configured to cause a portion of the insulating portion to vibrate through application of an ultrasound transmission pulse between the electrode in addition to the DC bias, to thereby transmit an ultrasound wave toward a subject;
   a receptor configured to receive an ultrasound echo from the subject;
   an image processor configured to produce an ultrasound image on the basis of a signal output from the receptor; and
   a discharger configured to apply sequential discharge pulses between the electrodes of the ultrasound transducer, wherein the sequential discharge pulses including a discharge pulse whose polarity is opposite that of an ordinary DC bias application voltage, in order to discharge a charge accumulated in the insulating portion between the electrodes, and further discharge pulses with a polarity reversing each time to thereby converge a transmission-reception sensitivity drift to zero.

2. An ultrasound diagnostic apparatus according to claim 1, wherein the discharger applies the discharge voltage between the electrodes while maintaining the absolute value of the discharge voltage constant.

3. An ultrasound diagnostic apparatus according to claim 1, wherein the discharger applies the discharge voltage between the electrodes such that the discharge voltage becomes equal to or higher than a collapse voltage at least one time.

4. An ultrasound diagnostic apparatus according to claim 1, wherein the discharger decreases an application time of the discharge voltage repeatedly applied between the electrodes.

5. An ultrasound diagnostic apparatus according to claim 1, further comprising a monitor configured to monitor an amount of charge accumulated in the insulating portion, wherein the discharger applies the discharge voltage between the electrodes on the basis of the amount of charge accumulated in the insulating portion.

6. An ultrasound diagnostic apparatus according to claim 5, wherein the monitor includes a storage configured to hold applied voltage historical information including history regarding the application voltage and application time of the DC bias applied between the electrodes; and
   the discharger applies the discharge voltage between the electrodes on the basis of the applied voltage historical information.

7. An ultrasound diagnostic apparatus according to claim 6, wherein the storage holds the sum of product of the application voltage and application time of the DC bias applied between the electrodes; and
   the discharger applies the discharge voltage between the electrodes when the sum of product reaches a predetermined threshold value.

8. An ultrasound diagnostic apparatus according to claim 7, further comprising a display configured to display at least one of history regarding the sum of product, a degree of reaching of the sum of product to the predetermined threshold value, and necessity and timing of the discharge processing of the discharger determined on the basis of the degree of reaching.

9. An ultrasound diagnostic apparatus according to claim 1, wherein the discharger discharges the charge at least when the ultrasound diagnostic apparatus is turned on or turned off, or when the transmission and reception of ultrasound waves to and from the subject is stopped.

10. An ultrasound diagnostic apparatus according to claim 1, wherein the discharger and the transmitter share a portion or the entirety of at least one of a pulse waveform producer configured to produce a pulse waveform, a pulse timing generator configured to determine timings at which the pulse waveform is generated, and a pulse amplifier configured to output a high voltage pulse.

11. An ultrasound diagnostic apparatus according to claim 1, wherein the discharger applies a voltage between the electrodes, the voltage being equal to or lower than a collapse voltage.

12. An ultrasound diagnostic apparatus according to claim 1, further comprising a reporter configured to report that the discharger is discharging the charge.

13. An ultrasound diagnostic apparatus according to claim 1, wherein the discharger discharges a charge accumulated in a diaphragm, which is a portion of the insulating portion.

14. An ultrasound diagnostic apparatus according to claim 1, further comprising a communicator configured to communicate with an external control apparatus provided at a location different from the location of the ultrasound diagnostic apparatus, wherein the discharger discharges the charge accumulated in the insulating portion between the electrodes on the basis of information from the external control apparatus.

15. An ultrasound diagnostic apparatus comprising:
an ultrasound probe equipped with an ultrasound transducer including a pair of electrodes and an insulating portion and a sacrificial layer provided in an area between the electrodes;
a DC-bias applier configured to apply a DC bias between the electrodes;
a transmitter configured to cause a portion of the insulating portion to vibrate through application of an ultrasound transmission pulse between the electrode in addition to the DC bias, to thereby transmit an ultrasound wave toward a subject;
a receptor configured to receive an ultrasound echo from the subject;
an image processor configured to produce an ultrasound image on the basis of a signal output from the receptor; and
a discharger configured to apply sequential discharge pulses including a discharge pulse whose polarity is opposite that of a DC bias application voltage of the DC bias, to the insulating portion and the sacrificial layer provided in the area between the electrodes, in order to discharge a charge accumulated in at least one of the insulating portion and the sacrificial layer in the area between the electrodes, the sequential discharge pulses further including discharge pulses applied a plurality of times with a polarity reversing each time to thereby converge a transmission-reception sensitivity drift to zero.

16. An ultrasound diagnostic apparatus comprising:
an ultrasound probe equipped with an ultrasound transducer including a pair of electrodes and an insulating portion and a sacrificial layer provided in an area between the electrodes;
a DC-bias applier applying a DC bias between the electrodes;
a transmitter configured to cause a portion of the insulating portion to vibrate through application of an ultrasound transmission pulse between the electrode in addition to the DC bias, to thereby transmit an ultrasound wave toward a subject;
a receptor configured to receive an ultrasound echo from the subject;
an image processor configured to produce an ultrasound image on the basis of a signal output from the receptor; and
a discharger configured to apply sequential discharge pulses of a discharge operation, to the insulating portion and the sacrificial layer provided in the area between the electrodes, in order to discharge a charge accumulated in at least one of the insulating portion and the sacrificial layer in the area between the electrodes, where a first discharge pulse of the sequential discharge pulses has a polarity opposite that of a DC bias application voltage of the DC bias and is applied for a predetermined period, and a succeeding sequential pulse has an opposite polarity to the polarity of the first discharge pulse and is applied for a lesser period than the predetermined period of the first discharge pulse, wherein subsequent discharge pulses of the sequential discharge pulses have a polarity reversing each time to thereby converge a transmission-reception sensitivity drift to zero.

17. An ultrasound diagnostic apparatus according to claim 16, wherein each subsequent succeeding sequential pulse of the discharge operation is applied for a lesser period than a preceding period of the preceding discharge pulse.

\* \* \* \* \*